(12) United States Patent
Skaria (10) Patent No.: US 11,951,885 B2
(45) Date of Patent: Apr. 9, 2024

(54) SIMULATOR AND METHOD OF TESTING SAFETY OF CAR TRAVEL FOR INFANTS

(71) Applicant: Mary Skaria, Sugarland, TX (US)

(72) Inventor: Mary Skaria, Sugarland, TX (US)

(*) Notice: Subject to any disclaimer, the term of this patent is extended or adjusted under 35 U.S.C. 154(b) by 636 days.

(21) Appl. No.: 17/088,984

(22) Filed: Nov. 4, 2020

(65) Prior Publication Data
US 2022/0134913 A1    May 5, 2022

(51) Int. Cl.
| | | |
|---|---|---|
| *B60N 2/26* | (2006.01) | |
| *A61B 5/00* | (2006.01) | |
| *A61B 5/08* | (2006.01) | |
| *A61B 5/145* | (2006.01) | |
| *B60K 35/00* | (2006.01) | |
| *B60N 2/04* | (2006.01) | |

(Continued)

(52) U.S. Cl.
CPC .............. *B60N 2/26* (2013.01); *A61B 5/0816* (2013.01); *A61B 5/14542* (2013.01); *A61B 5/6893* (2013.01); *B60K 35/00* (2013.01); *B60N 2/04* (2013.01); *G01C 21/3407* (2013.01); *G01P 13/00* (2013.01); *A61B 2503/04* (2013.01); *B60K 2370/152* (2019.05); *B60K 2370/16* (2019.05)

(58) Field of Classification Search
CPC ....... G01P 13/00; A61B 50/13; A61B 5/6893; A61B 5/6823; A61B 5/0816; G06Q 30/0255; A61M 16/0051; A61M 16/122; B60N 2/2824; B60N 2/26
See application file for complete search history.

(56) References Cited

U.S. PATENT DOCUMENTS

| | | | | |
|---|---|---|---|---|
| 4,326,513 A | * | 4/1982 | Schulz | A61M 16/0051 |
| | | | | 128/203.14 |
| 2008/0156328 A1 | * | 7/2008 | Taube | A61M 16/122 |
| | | | | 128/204.22 |
| 2016/0303969 A1 | * | 10/2016 | Akula | A61B 5/6893 |

(Continued)

FOREIGN PATENT DOCUMENTS

DE    102015013876 A1  *  5/2017   ........... A61B 5/6893

OTHER PUBLICATIONS

Arya, Renu , et al., "Is the infant car seat challenge useful? A pilot study in a simulated moving vehicle", Arch Dis Child Fetal Neonatal Ed 2017; F136-F141.

(Continued)

*Primary Examiner* — Yuri Kan
(74) *Attorney, Agent, or Firm* — Clayton, McKay & Bailey, PC (57) ABSTRACT

A simulator for testing a capacity of an infant to travel includes a car body, a back seat in the car body, a base of a car seat assembly secured to the back seat, an infant seat secured to the base, a plurality of sensors, a plurality of force applying actuators, and a control. One set of sensors in plurality of sensors may monitor parameters for a subject positioned in the infant including oxygen saturation, pulse, and respiratory rate. Another set of the plurality of sensors may monitor a position of the infant seat relative to the base and the subject relative to the infant seat. The control is configured to operate the plurality of force applying actuators to apply lateral, vertical, and linear forces to the back seat, the base, and the infant seat to simulate car travel relative to the subject.

18 Claims, 6 Drawing Sheets

(51) Int. Cl.
*G01C 21/34* (2006.01)
*G01P 13/00* (2006.01)

(56) References Cited

U.S. PATENT DOCUMENTS

| | | | | |
|---|---|---|---|---|
| 2019/0300020 A1* | 10/2019 | Alexiou | ................ | G06F 3/016 |
| 2020/0397526 A1* | 12/2020 | Williams | ............... | A61B 50/13 |
| 2020/0405078 A1* | 12/2020 | Martin | ............... | G06Q 30/0255 |
| 2022/0250513 A1* | 8/2022 | Mason | ................ | B60N 2/2824 |

OTHER PUBLICATIONS

Davis, NL, "Screening for cardiopulmonary events in neonates: a review of the infant car seat challenge", Journal of Perinatology (2015) 35, 235-240, Feb. 12, 2015.

Pilley, E., "The care seat: a challenge too far for preterm infants?", ADC Fetal & Neonatal Edition, Jan. 17, 2020.

Shah, Malika D., et al., "Clinical Outcomes Associated with a Failed Infant Car Seat Challenge", The Journal of Pediatrics, vol. 180, Jan. 2017.

* cited by examiner

SIMULATOR AND METHOD OF TESTING SAFETY OF CAR TRAVEL FOR INFANTS

BACKGROUND

More than 12% of infants in the U.S. are born prematurely every year. Many physiological monitoring studies indicate preterm infants can be susceptible to experiencing episodes of oxygen desaturation, apnea, or bradycardia when seated in standard infant car seats.

The American Academy of Pediatrics ("AAP") recommends that all preterm infants be assessed for cardiorespiratory stability in the context of car travel prior to discharge. More specifically, the APP recommends that pre-term infants undergo what is commonly referred to as "the car seat challenge" prior to discharge to prevent morbidity and mortality. Thus, the car seat challenge is broadly employed in hospitals across the U.S. to evaluate cardiorespiratory stability of preterm infants.

However, although some form of a car seat challenge test is employed by many hospitals, there is a dearth of widely accepted guidance related to procedures and requirements for such tests. No one form of a car seat challenge has been approved by a national organization such as the AAP, or widely accepted by hospitals or members of the medical community. Thus, universal guidelines for implementing a car seat challenge that tests a preterm infant's cardiorespiratory stability during car travel are not readily available.

In some examples, car set challenges may involve: a baby being connected to heart rate and respiratory rate monitors; the baby being securely seated in a car seat; the car seat being placed on the floor or other flat surface; and the baby being observed for 90 minutes for instances in which the baby exhibits instances of apnea, bradycardia, or oxygen desaturation. However, such testing procedures have several flaws.

First, with the car seat statically resting on a floor or other surface which is also static, the applicability to actual car travel is minimal. In fact, the validity of such a test as a means of distinguishing between an infant who can safely travel in a car or one who is at risk of adverse effects during such travel has not been proven or otherwise recognized. Thus, the test has very limited predictive value as to how safe car travel is for infant that may have been born before a 37-week gestational age and/or suffer from or be susceptible to: hypotonia; airway instability; ongoing cardiac limitations; neurological impairments; and a need for oxygen supplementation post-discharge.

Second, since the baby is placed on the floor for 90 minutes, there are opportunities for actual or potential injury to the baby and other. Such a test is likely to be conducted in a newborn intensive care unit ("NICU") where clinicians and visitors are frequently present, moving around, and may be carrying equipment or supplies. Thus, preterm infants undergoing a car seat challenge where the car seat is resting on the floor run the significant risk of being tripped over or having objects fall on them.

Accordingly, a need exists for a device, test procedures, and test requirements for safely conducting a predictive evaluation of an infant's response to a moving environment while seated in a car seat. More specifically, a need exists for systems and methods that can test and be used to predict a preterm infant's cardiorespiratory behavior and overall capacity to travel without significant risk while he or she travels from a hospital where they were born to their home.

SUMMARY

Examples described herein include systems and methods for testing a capacity of an infant to travel. In particular, examples described herein include systems and methods that can be employed to simulate the motion that an infant may experience in a car seat assembly when traveling in a car for the first time from a hospital to a destination, such as the infant's home. As a result, the systems and methods described herein are particularly advantageous for testing the capacity of an infant to travel in a car (in an infant car seat assembly) where the infant: is preterm; and/or was born with a congenital anomaly, a compromised cardio respiratory system, a genetic abnormality, or hypotonia; and/or requires, and therefore must travel with, oxygen or nasogastric tubes respectively placed in front of, or inserted into their nostrils.

In one example, a simulator for testing a capacity of an infant to travel may include a car body, a back seat positioned within the car body, a base of a car seat assembly secured to the back seat, and an infant seat of the car seat assembly may be secured to the base. In one example the simulator may include a plurality of sensors configured to monitor parameters including an oxygen saturation and a respiratory rate of a subject positioned in the infant seat. In another example, the plurality of sensors may monitor a position of the infant seat relative to the base or the subject relative to the infant seat. The simulator may also include a plurality of force applying actuators, and each of the plurality of force applying actuators may be configured to apply a lateral, vertical, or linear force respectively to the back seat, the base, or the infant seat. Further, the simulator may include a control that is configured to operate the plurality of force applying actuators to apply the lateral, vertical, and linear forces to the infant seat to simulate car travel relative to the subject.

In another example, a car seat assembly for testing a capacity of an infant to travel includes a base, an infant seat configured to be secured to the base, a first set of sensors, a second set of sensors, and a plurality of for applying actuators. In one example, the first set of sensors may be configured to monitor parameters including an oxygen saturation and a respiratory rate of a subject positioned in the infant seat. The second set of sensors may be configured to monitor a position the infant seat relative to the base and a position the subject relative to the infant seat. The plurality of force applying actuators may be disposed in the infant seat and the base, and each of the plurality of force applying actuators may be configured to apply a lateral, vertical, or linear force. In addition, the simulator can include at least one hub connected to the first set of sensors, the second set of sensors, and the plurality of force applying actuators. The hub may put the first set of sensors, the second set of sensors, and the plurality of force applying actuators in communication with a control. In one example, the control may be configured to receive data from the first set of sensors and the second set of sensors, and operate the plurality of force applying actuators to apply the lateral, vertical, and linear forces to the infant seat to simulate car travel relative to the subject based on the data received.

In another example, a method for testing a capacity of an infant to travel may include providing a simulator including a car body, a back positioned in the car body, a base of a car seat assembly secured to the back seat, an infant seat secured to the base, a plurality of sensors, a plurality of sensors, and a control. The method may include receiving, with the control, subject information including a weight, a length, an age, and a gestational age at birth for a subject. In one example, simulation limits for a respiratory rate, oxygen saturation, and pulse of the subject may be generated for a simulation based on the subject information. The method may include positioning the subject in the simulator and checking, with the control and the plurality of sensors, vitals of the subject. In another example, the simulation may be implemented by operating, with the control, the plurality of force applying actuators to apply lateral, vertical, and linear forces to the infant seat. In addition, the vitals of the subject may be continuously monitored during the simulation with the plurality of sensors. In another example, the method can include stopping the simulation with the control based on at least one of an elapsed time for the simulation, and a comparison of the vitals of the subject and the simulation limits. In yet another example, stopping the simulation may be couple with issuing a stop alert with the control.

The examples summarized above can each be incorporated into a non-transitory, computer-readable medium having instructions that, when executed by a processor associated with a computing device, cause the processor to perform the stages described. Additionally, the example methods summarized above can each be implemented in a system including, for example, a memory storage and a computing device having a processor that executes instructions to carry out the stages described.

Both the foregoing general description and the following detailed description are exemplary and explanatory only and are not restrictive of the examples, as claimed.

DESCRIPTION OF THE EXAMPLES

Reference will now be made in detail to the present examples, including examples illustrated in the accompanying drawings. Wherever possible, the same reference numbers will be used throughout the drawings to refer to the same or like parts.

However, reference numerals and terminology used herein are for the purpose of describing particular aspects only and are not intended to be limiting. For example, as used herein, the singular forms—"a," "an," and "the"—are intended to include the plural forms as well, unless the context clearly indicates otherwise. As another example, recitation of ranges of values herein are merely intended to serve as a shorthand method of referring individually to each separate value falling within the range. Unless otherwise indicated herein, and each separate value is incorporated into the specification as if it were individually recited herein.

Furthermore, it is noted that any one or more aspects or features described with respect to one example, may be incorporated in different examples described herein, although not specifically referred to or otherwise described relative thereto. That is, all examples and/or features of any aspect described herein can be combined in any way and/or combination. Thus, all methods described herein can be performed in any suitable order unless otherwise indicated herein or otherwise clearly contradicted by context.

Examples described herein relate to a simulator for testing a capacity of an infant to travel that can include a car body, a back seat in the car body, a base of a car seat assembly secured to the back seat, an infant seat secured to the base, a plurality of sensors, a plurality of force applying actuators, and a control. One set of sensors in plurality of sensors may monitor parameters for a subject positioned in the infant including oxygen saturation, pulse, and respiratory rate. Another set of the plurality of sensors may monitor a position of the infant seat relative to the base and the subject relative to the infant seat. The control is configured to operate the plurality of force applying actuators to apply lateral, vertical, and linear forces to the back seat, the base, and the infant seat to simulate car travel relative to the subject.

Figure 1:
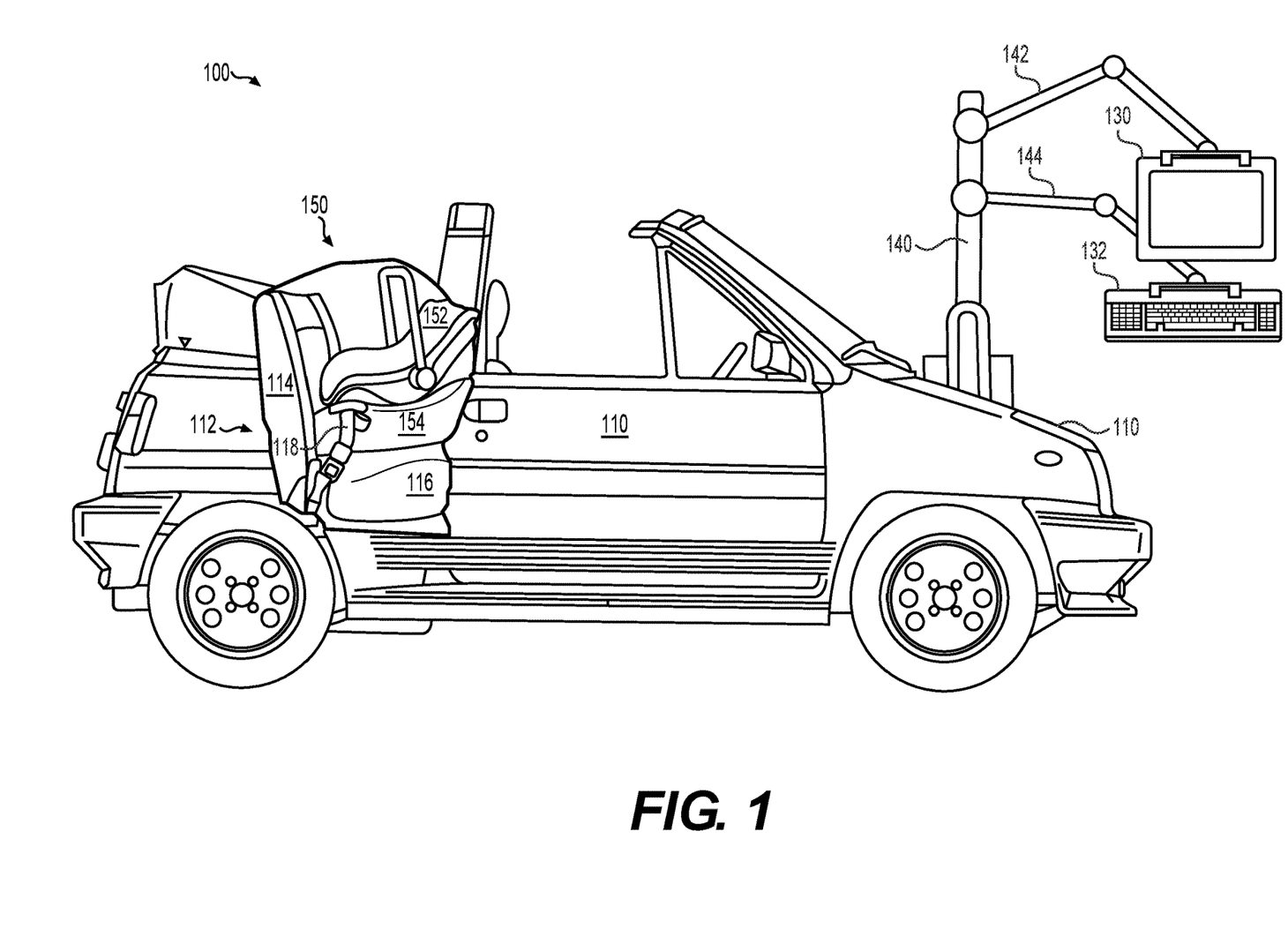
FIG. 1 illustrates a side elevation view of an exemplary simulator for testing an infant's capacity to travel in a car while positioned in a car seat, with a partial cutaway to show a car seat assembly of simulator.

FIG. 1 illustrates a side elevation view of an exemplary simulator for testing an infant's capacity to travel in a car while positioned in a car seat, with a partial cutaway to show a car seat assembly of simulator. As shown, the simulator 100 includes a car body 110, a user interface 130, and a keyboard or other data input device 132 infant, and a car seat assembly 150.

The car body 110 may be model after any type of vehicle suitable for driving while carrying an infant positioned in an infant seat secured to a back seat of the vehicle. In one example, the car body 110 may be a miniaturized version of a larger car. Further the car body 110 may include a stanchion 140 from which first and second arms 142, 144 extend and support the user interface 132 and data input device 132. More fundamentally, the car body 110 includes a back seat 112 commonly found in vehicles in which infants travel, which may include: a seat back 112 defined as a vertically extending component or cushion that supports a back of a passenger (hereafter referred to as "seat back 114"); and a seat cushion 116 provided as a bench, a bucket seat, a captains chair seat, or other type of lower torso and leg supporting component.

The back seat 112 provided in the car body 110 can be any type of seat found in a vehicle to which an car seat assembly 150 may be secured in a rear facing direction (i.e., a direction which orientates an infant to face a rear of a vehicle) according to accepted local, state, and/or government guidelines and/or regulations, such as those provided by the National Highway Traffic Safety Administration ("NHTSA"). In addition, the back seat 112 will be equipped with one or all of the following types of securement devices: a lap belt 118, an over the shoulder belt (not shown); tether anchors normally located above/behind a vehicle's back seat on a rear shelf, on a back of a vehicle seat, on a floor, a ceiling, or other locations as in lower anchors (not shown) that are provided between a back support and a bench or bucket seat of a back seat; a floorboard configured to support a vertical support leg extending from a car seat base, and the like. In one example, the various securement mechanisms may be provided and selectively used during an actual test based on a type vehicle an infant subject to the test is going to leave a hospital in.

The car seat assembly 150 includes an infant seat 152 a base 154, to which the infant seat 154 may be secured, as shown in FIG. 1. In one example, the base 154 and infant seat 152 can be combined into a single structure. In other examples, the infant seat 152 may be detachable from the base 154. In still other examples, the base 154 may be equipped with one or more securement systems respectively configured to receive and secure an infant seat of a particular design. Accordingly, the simulator 100 of the present disclosure may be used to test an infant's capacity to travel in a car while positioned in an actual car seat the infant will be positioned in during a car trip from a hospital to a home of the infant.

As described in more detail with reference to FIG. 2, force applying actuators are used to simulate travel in a car while an infant is positioned in a car seat assembly. Furthermore, various sensors are secured to the base 154, the infant seat 152, and a test subject to detect the test subject's vitals and position, as well as positions and movement profiles of the infant seat 152 and the base 154. In some examples, some of the force applying actuators and sensors may be detached from one version of the base 154 and/or the infant seat 152, and positioned on different versions of the same. In one example, each base 154 and infant seat 152 combination can be analyzed prior to a testing to determine the appropriate positions for the actuators.

Figure 2:
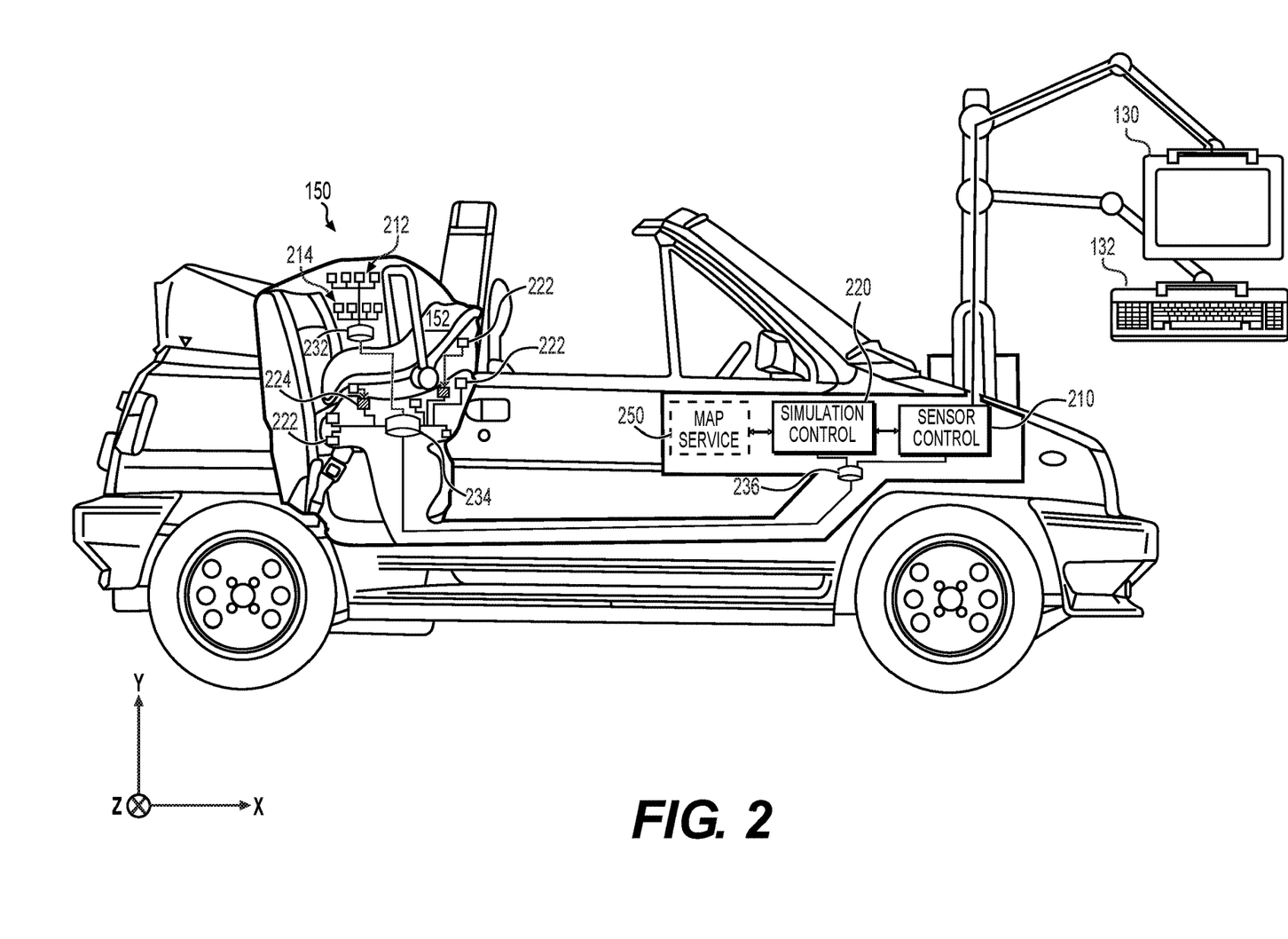
FIG. 2 illustrates a side elevation view of an exemplary simulator with partial cutaways to show exemplary system components for testing an infant's capacity to travel in a car while positioned in a car seat assembly.

FIG. 2 illustrates a side elevation view of the exemplary simulator 100 with partial cutaways to show exemplary system components for testing an infant's capacity to travel in a car while positioned in a car seat for infants. The system components of the simulator 100 include a sensor control 210, a simulation control 220, a first set of sensors 212, a second set of sensors 214, a plurality of force applying actuators 222 ("actuators 222"), and one or more adaptors 224.

The sensor control 210 is in communication with the user interface 130, the first and second sets of sensors 212, 214 (also referred to hereafter as "the sensors 212, 214"), and the simulation control. During a test, raw data detect by the first and second sets of sensors 212, 214 is transmitted to the sensor control, where the data is processed for presentation in the user interface 130 and transmission to the simulation control 220. In one example, the sensor control 210 can direct the simulation control 220 to modify operations of the actuators 222 based on data received from the sensors. In another example, the simulation control 220 may further process the data received from the sensor control and determine that a modification to the operation of one or more of the actuators is required.

It will be understood that the sensor control 210 and the simulation control 220 may be embodied in a single or separate computing devices as part of the simulator 100. In one example, a control defined by the sensor and simulation controls 210, 220 may include a physical computing device provided in the car body 110, the base 154, or the infant seat 152.

The first set of sensors 212 may include a various vital statistic-monitoring sensors for monitoring vitals of an infant positioned in the infant seat 152. In one example, the first set of sensors may include a pulse oximeter that monitors a subject's blood oxygen saturation. In some examples the pulse oximeter may be configured to also monitor a subject's heart rate (i.e., pulse), but in other examples, the first set of sensors 212 may include a separate sensor for this parameter. In another example, the first set of sensors can include a respiration sensor that monitors a breathing rate a relative depth of abdominal or thoracic breathing. In still other examples, the first set of sensors can include one sensor or a sub-set of sensors that are used to provide the sensor control 210 with data for different physiological parameters known in the art as being required to determine/detect respiratory failures considered to be instances of apnea.

Those of ordinary skill in the art will recognize that the first set of sensors include, at least, those sensors configured to monitor a subject for instances of apnea, bradycardia, hyperventilation, oxygen desaturation, an irregular heart beat, and various forms of respiratory distress. In particular, the first set of sensors 212 includes sensors specifically designed to monitor for these conditions in infants, and more specifically, in infants considered pre-term or premature—born at fewer than 37 weeks' gestational age.

The second set of sensors 214 may include one or more types of position sensors for monitoring: (1) general movements of a subject; (2) a position of a subject relative to the infant seat 152; (3) a position and movement of the infant seat 152 relative to the base 154; and (4) a position and movement of the base 154 relative to the back seat 112. In one example, the second set of a sensors can include hall sensors, accelerometers, gyroscopes, magnetometers, optical encoders, and the like which detect movement and/or positions of elements to which they are secured or are fixed relative to the movement of.

Information from the second set of sensors 214, as with the first set of sensors 212 can be transmitted through a wired or wireless connection to the sensor control 210 where that data can be processed. The sensor control 210 can package the processed data and transmit the same, depending on values of monitored parameters, to the simulation control 220. The processed data may be packaged with instructions from the sensor control 210 that cause the simulation control 220 to alter or stop various operations of the actuators 222. In another example, the sensor control 210 may be configured to recognize certain values for monitored parameters as triggers which cause the sensors 212, 214 to transmit the processed data related to those parameters to the simulation control 220. In turn, the simulation control 220 may be configured to recognize the values of those selected monitored parameters as indicating the occurrence of an event or condition during an ongoing test operation of the simulator 100 that requires a modification or stoppage of the operations of one, more than one, or all the actuators 222. Examples of such events and conditions are discussed in more detail with reference to the method of FIG. 4.

In addition to the types of vital statistic-monitoring and position sensors described above, either of the first or second set of sensors 212, 214 can include a video camera. Such a camera may have controllable viewing angle and focus and thereby be used to obtain a continuous visual of a subject during a testing session.

In one example, data including instructions for operation (e.g., sampling frequency, sensitivity, reporting frequency) from the sensor control 210 and raw or processed data for monitored parameters obtained by any of the sensors 212, 214 may be transmitted via wired connections between the sensors 212, 214 and the sensor control 210. Cables and wires connecting these components can be run through conduits extending from first, second, and third hubs 232, 234, 236. In another example the raw or processed data can be transmitted through a wireless connection between the sensor control 210 and each of the sensors 212, 214. Thus, each of the first and second set of sensors 212, 214, as well as the sensor control 210, may be equipped with a wireless transmitter of some type. More specifically, each of the sensors 212, 214 may include one or more wireless data transmitting devices configured to send and receive data with one or more wireless data transmitting devices of the sensor control according to a respective wireless communication protocol (e.g., Bluetooth, Bluetooth Low Energy, Zigbee, a Wifi chip, etc.) both devices implement.

In another example, at least one of the first and second hubs 232, 234 may be equipped with receivers that are compatible with the different sensors of the first and second sets of sensors 212, 214. Further, one or all the first, second, and third hubs may be equipped with a wireless data transmitting device. Accordingly, the first and second sets of sensors 212, 214 could be wired to the first hub 232 or the second hub 234, and either of the hubs may be configured to establish a wireless connection with each other, the third hub 236, or the sensor control 210 for wireless transmission of data collected by the sensors.

The first set of sensors 212 monitor a subject's vitals, and second set of sensors 214 monitor positions and movements of the subject and various components of the car set assembly 150 during testing that includes various operations of the actuators 222. The actuators 222 are configured to apply linear forces and cause movements along an X-axis (i.e., front to rear direction of the car body 110 and vice versa. Further, the actuators 222 are positioned and configured to apply lateral forces and cause movements along a Z-axis, as well as applying vertically oriented forces and cause movements along a Y-axis. In another example, the actuators 222 may apply forces to, for example the infant seat 152, along and between XY-, YZ-, and XZ-planes of a three-dimensional coordinate system—thus including applications of force and resulting movements along the X-, Y-, and Z-axes previously mentioned.

In one example, the actuators may include some type of prime mover, fluid pump or motor, hydraulic or pneumatic cylinder, or other mechanism that can be controlled to apply a force: (1) on a one time basis (e.g., to simulate some type of impact or irregularity in a road such as a pot hole); (2) cyclically according to some frequency; (3) on a random basis; and/or (4) to cause (i) controlled, (ii) vertical, horizontal, and/or lateral, (iii) gliding, abrupt, and/or vibratory movements, in order to mimic bumps, undulations, certain hazards (e.g., potholes) on a road. In one example, one or more actuators may include: a solenoid driven piston; a motor, a shaft driven by the motor, and a cam or type of asymmetric force applicator mounted to the shaft; piezoelectric strips; magnets that can be controllably energized to vary polarity and electromagnetic force (e.g., as in pairs of opposing magnets can be operated to attract and repel one another); pads or pockets in fluid communication with some type of pump and which expand an contract when a fluid such as a liquid or air are conveyed thereto or withdrawn therefrom; and other types of force applicators of the like and/or known in the art.

In yet another example, at least one actuator can include a hydraulic or pneumatic cylinder with a first end attached to the cylinder fixed to either the infant seat 152 or the base 154. A second end of this actuator may include a rod end of a piston that extends and retract within the cylinder. This second end may include some type of structural feature configured to fixedly or detachably attach to a corresponding structural feature of the other of the base 154 or the infant seat 152 not engaged with the first end of the actuator. With the inclusion of this actuator, an angle of the infant seat relative to the base 154 and the X-axis (see FIG. 2) may be set to a particular value or varied during a testing session. For example, the infant seat 152 may be positioned at an angle of 0° to 45° relative to the X-axis. It will also be understood that this actuator may be used to rapid change an angle of the infant seat were there a situation where a subject experiencing an event that could lead to the subject being in distress.

In another example, the actuators 222 for the infant seat 152 may be coupled to adapters 224 when the infant seat 152 is secured to the base 154. Power may be supplied to these actuators by the simulation control 220 or a separate power supply through the adaptors 224. In one example in which the actuators 222 communicate with the simulation control 220 through a wired connection, the adaptors 224 may put the infant seat actuators 222 in data transmission-enabling communication with the simulation control 220. In another example, data including instructions for operation from the simulation control 220 and operational feed back from any of the actuators 222 may be transmitted back and forth through a wireless connection between the simulation control 220 and each of the actuators 222. In another example, a wireless connection may be established between the simulation control 220 and a second hub 234 connected to the actuators 222 through wired and/or wireless connections like the first and second sets of sensors 212, 214 and the sensor control 210.

The sensor and simulation controls 210, 220 may be provided by separate or a single computing device including a processor, a memory storage, and a non-transitory computer-readable medium containing instructions that are executed by the processor. Together, the simulation and sensor controls 210, 220 direct and/or monitor the operations of the first and second set of sensors 212, 214, the actuators 222, the adapters 224, and the user interface 152 so as to operate the simulator 100 to perform the methods described herein.

As previously discussed, wireless connections can be established between the first and second set of sensors and the sensor control 210, as well was between the actuators 222 and the simulation control 220. In addition, various types of wireless data transmission protocols as previously mentioned, may be used to establish these wireless connections directly between the sensors, actuators, and controls. In another example, wireless communication between these components may be facilitated over a diversified network through an internet or a cellular connection. Furthermore, the simulation and sensor controls 210, 220 may be provided by one or more physical servers and/or cloud-based virtual servers that support the operations of the sensors and actuators. In addition, any computing device providing the simulation and sensor controls 210, 220 can employ software-based tools through which a user can monitor, manage, update, stop, or modify aspects of a testing session (e.g., change a magnitude and/or frequency of a force applied to the infant seat 152).

In another example, the simulator 100 can include a map service 250 or otherwise be configured to access a map service to provide route information to the sensor and simulation controls 210, 220. Either of the controls 210, 220 may be configured to cause the user interface 130 to display a data input field where an address for a subject of a testing session can be input. Further, either of the controls 210, 220 can transmit the address to the map service 250 along with a current location or address of where the simulator 100 is located. The map service 250 can determine one or more routes between the address of the subject and the address of the simulator 100, and provide route information for each of the routes to the simulation control 220.

As described with reference to FIG. 5, a route profile can be derived for each of the routes an encompass the types of roads, number of stop lights, topography, road construction, detours, traffic, scheduled time of travel, and other elements or route characteristics that will may be encountered while driving on the route to the subject's address. In turn, the simulation control 220 can apply predetermined rules or machine-learning-based algorithms designed to measure risk with respect to car trave for an infant, and in particular risk for a preterm infant, to determine a risk profile score for each route.

In one example, sensors and actuators that placed on the infant seat 152 may be detachable, and the base 154 may be design as a universal base configured to be able to receive a large number of types of infant seats. In another example, the actuators and adaptors may be detachable from the base. As a result, in some examples the infant seat 152 or the car seat assembly 150 may be interchanged with an infant or car seat assembly that responsible parties for a subject intend to use in transporting the subject in a vehicle.

Figure 3:
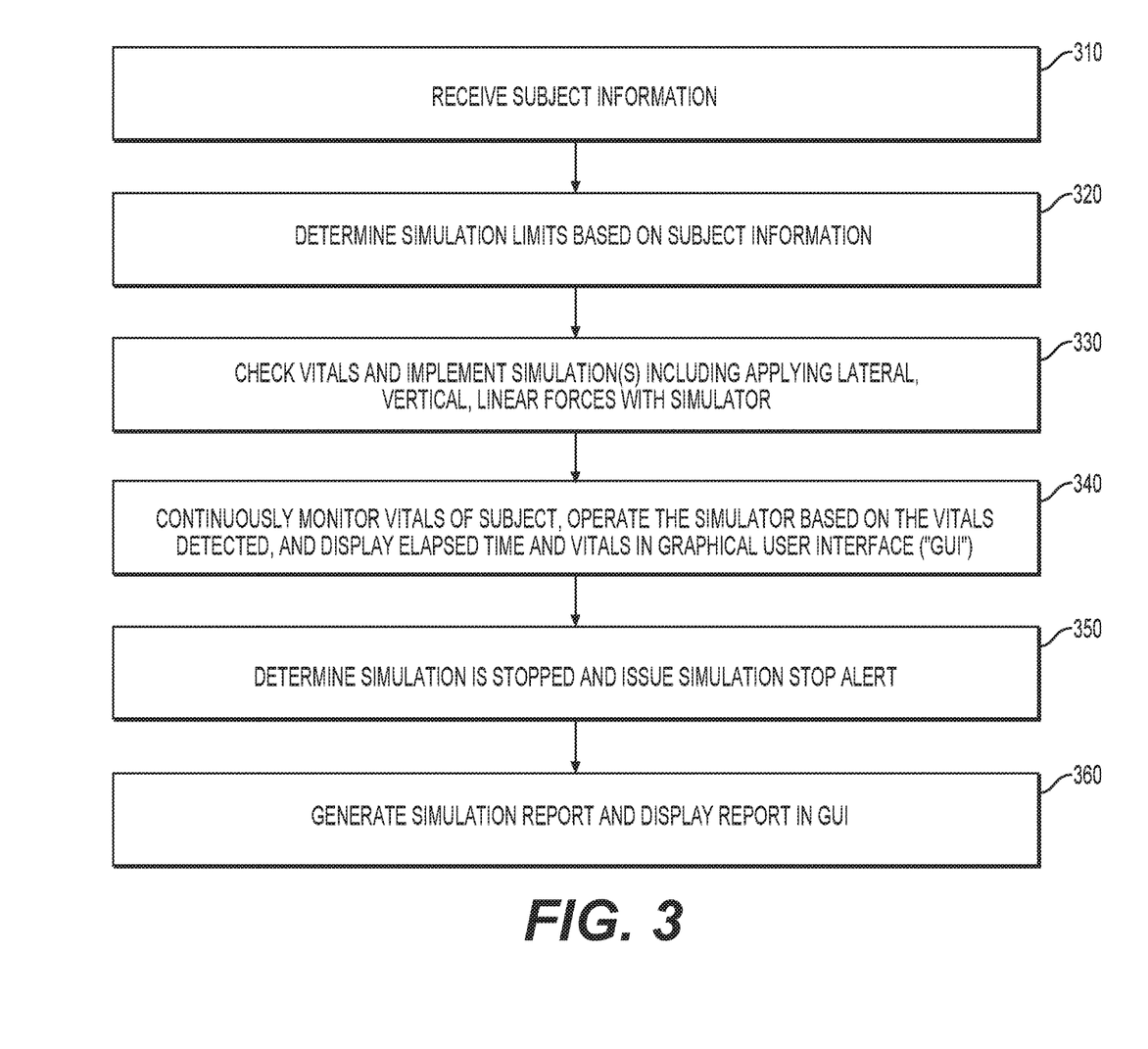
FIG. 3 is a flowchart of an example method for testing an infant's capacity to travel in a car while positioned in a car seat assembly.

FIG. 3 is a flowchart of an example method for testing an infant's capacity to travel in a car while positioned in a car seat assembly. In stage 310, information about a subject can be received by a simulator with, for example, a sensor control or a simulation control as described herein. Subject information can include a subject's name, length, blood type, current weight, head-size, average heart rate, average respiratory rate, age (in days), sex, weight at birth, and any other vital statistic typically monitored for infants, and more specifically for pre-term infants.

At stage 320, the simulator 100 can determine simulation limits based on the subject information received in stage 310. The simulation limits will necessarily include a preset time corresponding to a total time for a simulation, and thresholds for vital statistics monitored by sensors. Regarding time, in one example, stage 320 can include determining maximum duration for a standardized simulation, as well as a maximum time for a route mimicking simulation. A total simulation time can, in some examples, be equal to the sum of these two maximum durations.

Regarding thresholds for vital statistics, these simulation limits can be determined by the simulation control by referring to one or more lookup tables that associate measured physical (e.g., height, weight) and biological (e.g., blood-type, sex, average heart rate) with limits for certain categories of vital statistics (e.g., $O_2$ saturation %). In another example, the simulator 100, via the simulation control or other computing device, may employ various algorithms that relate certain characteristics to particular vital statistics. In one example, threshold values are determined for at least an $O_2$ saturation (%), minimum and maximum pulse rates (bpm—beats per minute), minimum and maximum respiratory rates (bpm—breaths per minute), and maximum deviation for a position of the subject's head or body from a predetermined normalized position.

In stage 330, the simulator 100 checks vital statistics of the subject prior to initiating a simulation by polling sensors, such as the first and second set of sensors 210, 220 for the simulator 100, which measure these parameters for the subject. Where readings from the sensors indicate vital statistics for the subject are all appropriately above or below corresponding simulation limits determine in stage 320, a simulation may be initiated. Accordingly, the simulator 100 begins and continues to apply lateral, vertical, and linear forces to an infant seat of a car seat assembly in which the infant is positioned.

In one example, a simulation implemented in stage 330 may involve operating the actuators to simulate a trip, relative to a subject in the simulator, in which: (1) a vehicle travels at a speed in the range of 25 miles per hour (mph) to 30 mph; (2) the vehicle periodically encounters bumps or other irregularities in the road; and (3) the subject (infant) is positioned at angle in a range of 40° to 45° relative to an X-axis. The subject may be positioned at the angle mentioned above by virtue of an actuator that includes, for example, a cylinder and reciprocating piston or shaft, which is operated to position the infant seat 152 at a particular angle between 40° and 45° relative to either the base 154, the X-axis, or an engagement surface of the base 154.

At stage 340, the simulator 100 continuously monitors the vitals of subject by polling sensors. In addition, the simulator 100 of the present disclosure may modify or stop operations of one, or more, or all of a plurality of force apply actuators, such as the actuators 222 illustrated in FIG. 2, based on the readings from the sensors. As explained in more detail with reference to FIG. 4, the simulator 100 can modify or a stop a simulation in one or more ways based on a type of stop or potential stop condition. Any modification or stoppage of an ongoing simulation can be coupled with an alert of a respective type. Stage 340 may also include the simulator 100 displaying an elapsed time and readings for the monitored vitals in a graphical user interface ("GUI"). In one example, a user interface such as the user interface 130 of the simulator 100, may be provided and configured to display a GUI, such as the GUI discussed with reference to FIG. 6.

In stage 350, the simulator 100 can determine a simulation has stopped, either due to a preset time elapsing or a stop condition, and issue simulation stop alert. Subsequently, a report for the now-stopped simulation may be generated in stage 360 and display in a GUI and/or transmitted to one or more computing devices for review by a clinician (e.g., a doctor, nurse, simulator technician).

Figure 4:
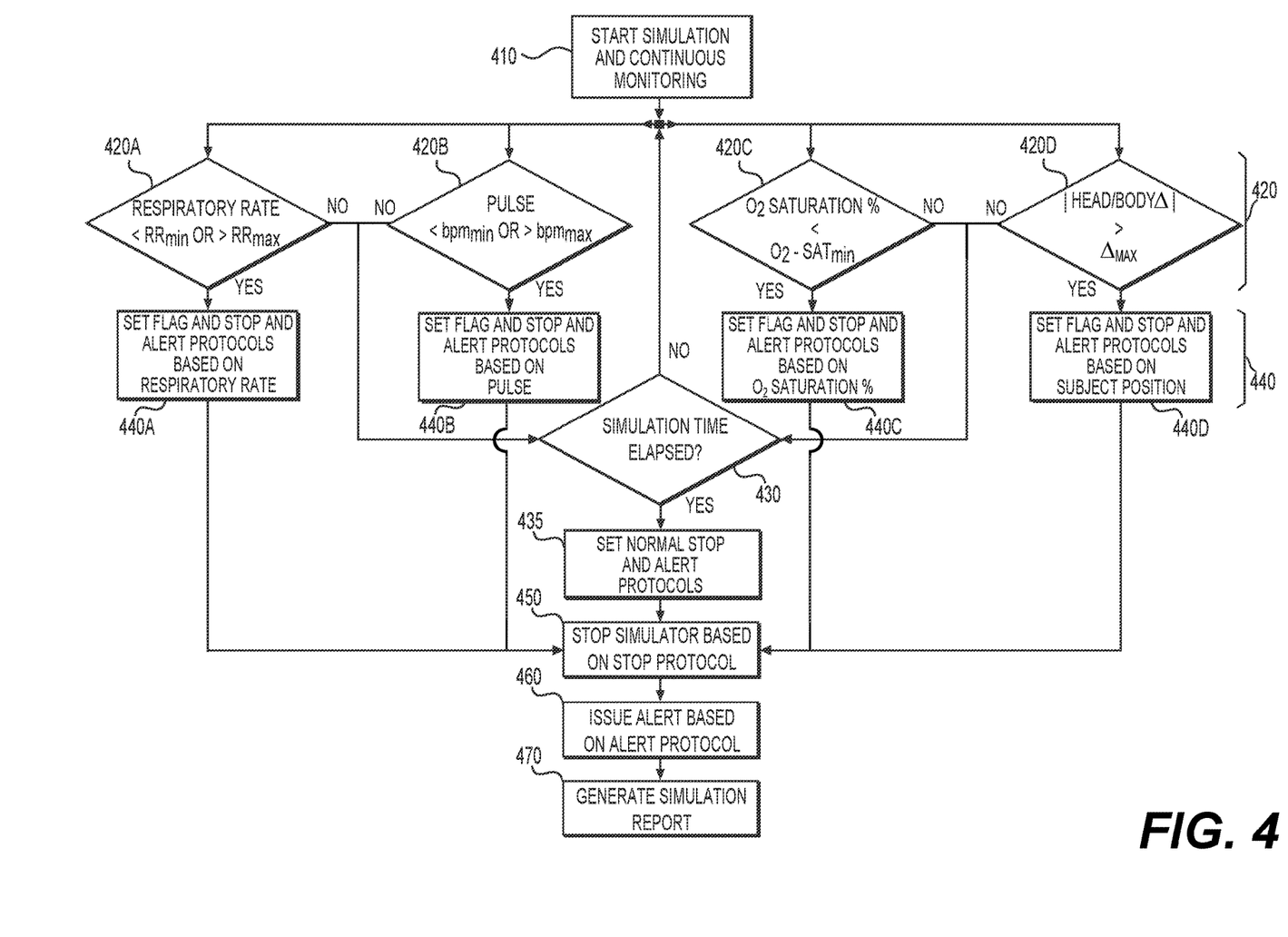
FIG. 4 is a flowchart of an example method for continuous monitoring and implementing safety protocols as part of testing an infant's capacity to travel in a car.

FIG. 4 is a flowchart of an example method for continuous monitoring and implementing safety protocols as part of testing an infant's capacity to travel in a car. In stage 410, a simulation may be initiated and sensors, such as the sensors 212, 214 in FIG. 2, can begin to continuously operate and provide raw or processed data to a control, such as the sensor control 210. Concurrently, actuators may begin continuously applying forces to an infant seat, a base, and a back seat as described herein.

Stage 420 includes stages 420A, 420B, 420C, and 420D. At stage 420A, a current reading for a subject's respiratory rate is compared to minimum and maximum respiratory rates established in stage 320. Likewise, a pulse detected for the subject is compare to minimum and maximum thresholds in stage 420B. At stage 420C, a detected $O_2$ saturation is compared to a minimum threshold, whereas a head and body position deviation is compared to a maximum threshold in stage 420D. Stags 420A, 420B, 420C, and 420D arranged on a same level of the flowchart illustrated in FIG. 4 to indicate that evaluations respectively executed therein can, and preferably do, occur simultaneously. Although each the evaluations may be executed in a series.

Where the simulator 100 determines that none of the criterium in stage 420 are met, an elapsed time for a current simulation may be reviewed in stage 430. Where a preset total time for the simulation has not entirely elapsed, the simulator 100 can repeat the execution of stage 420 again like a feedback loop. On the other hand, if a total time has elapsed, the simulator 100 will set normal stop and alert protocols to be executed in stage 450.

However, if any of the criterium for any one of the evaluations performed in stage 420 is met, the simulator 100 will initiate a process for stopping a simulation in stage 440. Stage 440 includes stages 440A, 440B, 440C, or 440D, each stage being specific to a threshold that has been exceeded or which a corresponding parameter has fallen below. In each of the stage 440A, B, C, and D a status of a flag is set to active for the purposes of carrying out additional method steps. In particular, the simulator 100 refers to a status of the flag, for example, in the method of FIG. 5 to determine if a route-based simulation can be implemented. In effect, the flag serves as a reference point that causes a control or other component of the simulator 100 to recognize that current stoppage of the simulator 100 due to a stop condition being met or exceeded. This serves the dual purpose of ensuring that a new simulation is not initiated for a subject whose capacity to undergo even a standardized simulation has been deemed to be insufficient, and efficient operation of the simulator 100 (i.e., the simulator 100 only operates when it is supposed to).

Turning to the specific stop and alert protocols that may be issued in stage 440, the simulator 100 is configured to stop a simulation in manner that accounts for a type of distress or other condition of the subject. In addition to setting the flag, in stage 440A, stop and alert protocols are generated based on respiratory rate. Depending on whether a current detected respiratory rate of a subject is below a minimum threshold or above a maximum threshold, the stop and alert protocols may differ. For example, if below a minimum threshold, a condition of the subject may require immediate attention, while at the same time, a sudden stop of the simulation may not increase a risk to, and may in fact be the safest option for, the subject. Accordingly, the alert protocol may include a combination of loud and high intensity lights and sounds, and may be coupled with a stop protocol that includes an immediate stop of the simulator 100.

On the other hand, where the subject's respiratory rate is above a maximum threshold, a loud and obtrusive alert coupled with a sudden stop of the simulator 100 may exacerbate the condition of the subject. The simulator 100 is configured to recognize a condition of the subject an implement alert and stop protocols that avoid startlingly the subject to a degree that he or she may be at risk of hyperventilating. Accordingly, the stop protocol for this condition may include a gradual winding down of force applying activity by actuators, and some form of visual alert presented on a user interface. In addition, the alert protocol may include transmitting a signal to an operator's phone or pager-like devices dedicated to operate in conjunction with the simulator 100.

In stage 440B, stop and alert protocols are generated based on a pulse detected for the subject. As with respiratory rate, depending on whether a current detected pulse of a subject is below a minimum threshold or above a maximum threshold, the stop and alert protocols may differ. In one example, the stop and alert protocols for the subject's pulse being below the minimum threshold may be the same or a slight variation of the stop and alert protocols generated when the subject respiratory rate falls below a respective minimum threshold. Stop and alert protocols generated when the pulse is above a maximum threshold may likewise be similar to those generated when a detected respiratory rate is above a respective maximum threshold.

In stage 440C, stop and alert protocols are generated based on $O_2$ saturation being below a minimum saturation limit determined in stage 320. As one of ordinary skill in the art will recognize, hemoglobin is an element in a person's blood that binds to oxygen and carries that oxygen to different parts of the body (e.g., organs, tissue, cells). Low oxygen saturation is a condition in which hemoglobin is not sufficiently saturated with oxygen, and can result from issues with a person's, here and infant's, respiratory system. Here again is a situation that in one example, the simulator 100 can be configured to recognize as one in which a sudden stop of the simulator 100 may present a risk to a subject. Accordingly, in stage 440C the simulation control, for example, may generate a stop protocol that provides a gradual decline in actuator activity until coming to a final stop. The decline in activity may be more or less rapid in comparison to those rates of decline implemented for high respiratory rate or high pulse conditions.

In stage 440D, the stop and alert protocols based on a head or body position deviation (A) being greater than a maximum deviation (Amax). More specifically, an absolute value of the head or body position deviation may be compared to the maximum deviation. However, a sign (+/−) of the head or body position deviation from a neutral position may be determinative of the type of stop and alert protocols that are generated. Further, whether or not the position deviation stems from a subject's head or body (e.g., torso) may also be used by the simulator 100 to determine the stop protocol.

For example, where the deviation concerns a subject's head, a deviation greater than the maximum deviation, whether negative or positive relative to a neutral position, may indicate that the subject is at risk of obstructing their airway due to angle of their head relative to their torso. In such a situation, stop and alert protocols may include an immediate stoppage of a simulation and an intense audio and visual alert.

Other situations which the simulator 100 is configured to recognized based on body and head position deviation may require a gradual stop. For example, a detected negative deviation of a subject's body relative to the neutral position may be greater than the maximum deviation limit determined in stage 320. This may indicate the subject is slouched down within an infant seat to a degree that a harness holding subject within the infant seat is at risk of choking the subject and impinging the subject's airway. It will be noted that the second set of sensors 214 may include position sensors attached to various components of the infant seat and a subject to measure distances between those components (e.g., a harness) and body parts (e.g., a neck) of the subject. Turning back to the situation described above, the simulator 100 may be configured to generate a stop protocol based on a recognition that a sudden stop could cause a sudden movement of the subject with negatively affects (e.g., the sudden movement may place the subject at greater risk of having their airway impinged by a harness). Accordingly, the stop protocol for this situation may include a gradual stoppage of force application by the actuators.

On the other hand, a body position positively deviating from a neutral position may indicate the subject in not sufficiently secured within the infant seat. As a result, to avoid place the subject as risk of experiencing large ranges of movement due to the subject not being sufficiently restrained, the simulator 100 may generate a stop protocol that includes an immediate stop of a simulation.

At stage 450, the simulator 100, via the simulation control 220 for example, stops the simulator 100 and ends a simulation according to the stop protocol generated in stage 435 or stage 440. In one example in which more than one condition evaluated in stage 420 is satisfied, stage 450 can include selecting a stop protocol associated with simulation limit deemed to be more critical from standpoint of a subject's safety. In stage 460, the simulator 100 can issue an alert based on an alert protocol generated in stage 435 or 440 and corresponding to the stop protocol implemented in stage 450. As noted above, together with the sensor control 210 and the simulation control 220, the actuators 222 can generate (i) controlled, (ii) vertical, horizontal and lateral, (iii) gliding, abrupt, cyclical, and/or vibratory movements to mimic irregularities on a road and/or a speed of travel, such as for example. Furthermore, in stage 450, the simulator 100, based on stage 440A, 440B, 440C, or 440D, can stop a simulation and the movements of the actuators and infant seat, as soon as there an indication that a subject may be reaching a point beyond which the subject may become distressed.

At stage 470, report including the readings obtained from sensors and forces applied by actuators can be generated for the simulation stopped in stage 450. In one example, the simulation report can be displayed in a dashboard as described with reference to FIG. 6.

Figure 5:
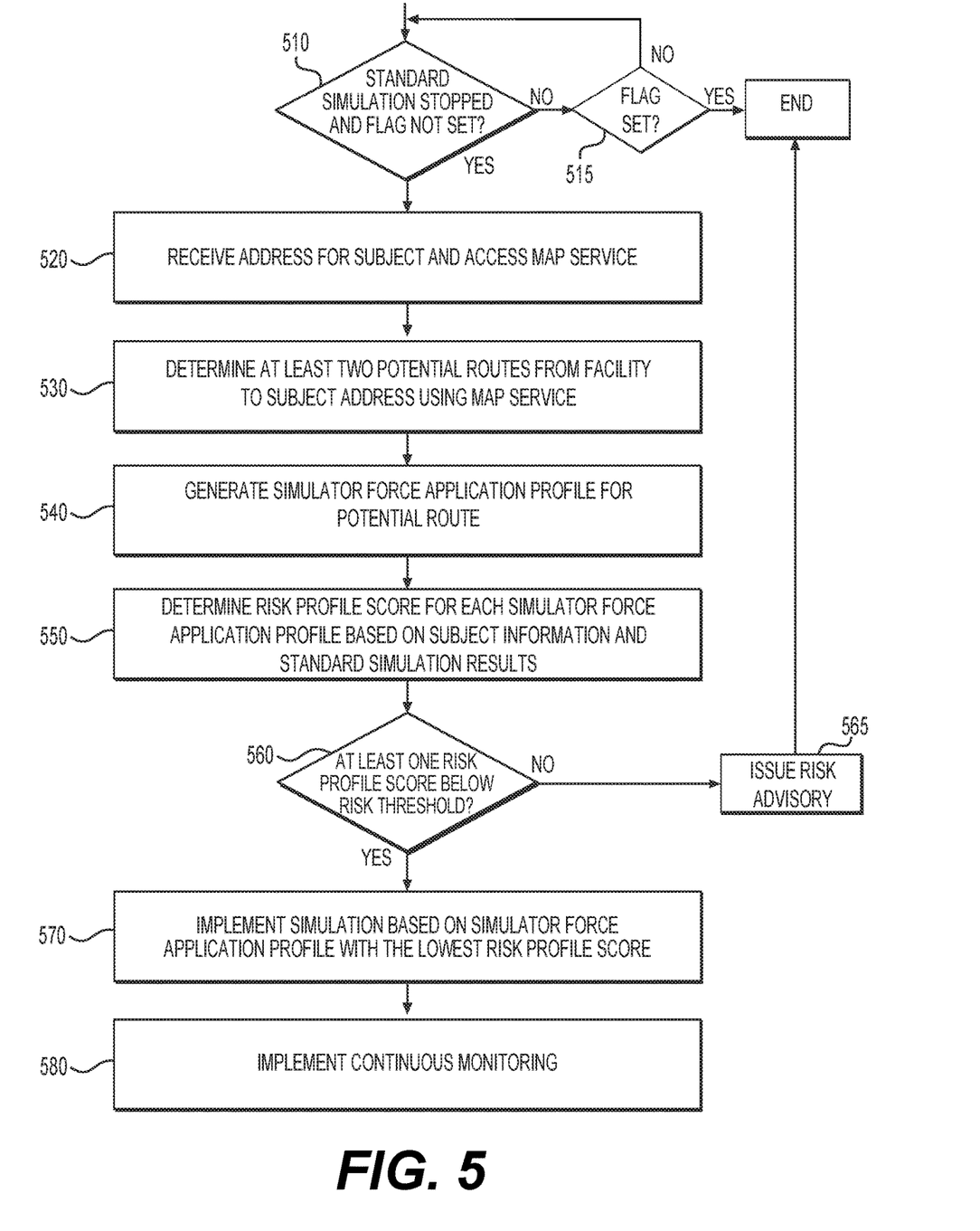
FIG. 5 is a flowchart of an example method for conducting multiple types of simulations as part of a procedure for testing an infant's capacity to travel in a car.

FIG. 5 is a flowchart of an example method for conducting multiple types of simulations as part of a procedure for testing an infant's capacity to travel in a car while positioned in a car seat assembly. In stage 510, the simulator 100, via the simulation control 220 for example, reviews a status of the flag and registers whether or not the simulator 100 has been stopped according to a normal stoppage condition in stage 435 (time for a standard simulation has elapsed). One of these conditions not being met could indicate that a standard simulation is not complete or has been stopped due to the occurrence of a stop condition being identified in stage 420. Accordingly, the simulation control 220 may again check the flag status in stage 515 and if not set to active, execute stage 510 like a feedback loop.

Where both conditions in stage 510 are met, the simulator can receive an address for a subject and access the map service in state 520. The simulation control 220, in one example can cause the user interface 130 to prompt an operator for the address and then receive a response input through the user interface 130 (via the data input device 132 or the user interface 130 itself where the user interface includes a touch screen).

At stage 530, the simulator 100, via the simulation control 220 for example, can determine at least two potential routes from facility to subject address using map service. In stage 540, generate simulator force application profile for each potential route. In one example, the simulation control maps out a series of force applications corresponding to those a subject may potential experience riding in a vehicle traveling on a give route. The force application profile with therefore estimate and project the forces that may be generated when a vehicle travels on a curved or winding road included in a route, or compensate for topography. In other examples, the force application profile with estimate potential forces that may be applied to a car seat assembly due to stop (e.g., stops at stop lights, eight ramps, parking, due to traffic, etc.).

At stage 550, the simulator determines a risk profile score for each simulator force application profile based on subject information and standard simulation results. In one example, the risk profile score can include a summation of scores assigned to various force application events along a route. In another example, the simulator 100 may access look up tables or use various algorithms to determine scores of these events based on their respective characteristics (e.g., curvature of path, speed limit before a stop, speed limit variance, total time of travel, etc.).

In stage 560, the simulator can compare the risk profile scores to a risk threshold value to determine if at least one risk profile score is below that risk threshold. This may indicate the subject may have the capacity to be transported in a vehicle along a route corresponding to that risk profile score. In the event no risk profile score is below the risk threshold, the simulator 100, via the simulation control 220 and the user interface 130 in one example, can issue risk advisory in stage 565. The risk advisory may include a breakdown of the force application events along the routes analyzed.

On the other hand, where at least one risk profile score is below the threshold, a corresponding simulator force application profile can be implemented in stage 570. In one example, the simulator force application profile with the lowest risk profile score may be implemented where there is more than one risk profiles score less than the risk threshold. In another example, the simulator force application profile with the highest risk profile score that is less than the risk threshold may be implemented. At stage 580, continuous monitoring according to stage 340, which can include stage 410 and the method of FIG. 4, can be implemented.

Figure 6:
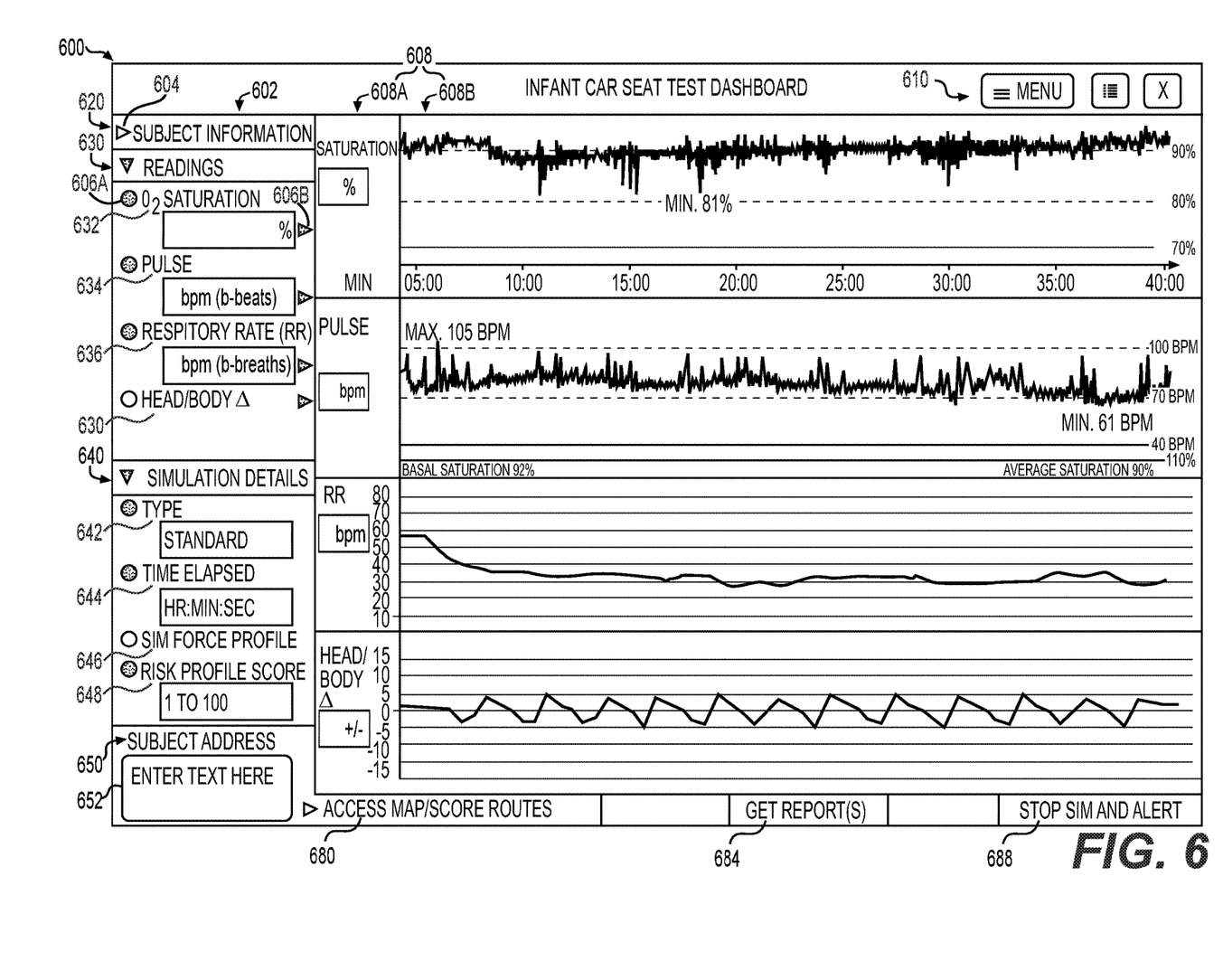
FIG. 6 is an illustration of an example graphical user interface ("GUI") of a console for implementing different simulations and reporting testing results according to various methods described herein.

FIG. 6 is an illustration of an example graphical user interface ("GUI") of a console for implementing different simulations and reporting testing results according to various methods described herein. More specifically, FIG. 6 illustrates an exemplary dashboard 600 for reviewing monitored parameters during a testing session in which the methods described herein are performed using a simulator according to the present disclosure, such as the simulator 100 of FIGS. 1 and 2. In one example, the dashboard 600 can provide a GUI for a clinician that includes a navigation menu 602, a console window 608, and an instrument panel 610. The instrument panel 610 may include selectable options for accessing a menu of additional options, changing a view of the dashboard, or closing some portion or view of the dashboard 600. It will be understood that the dashboard 600 provides an example of a GUI that one or both of the sensor control 210 and the simulation control 220 drive information to, and cause to be displayed in a user interface, such as the exemplary user interface 230 illustrated in FIGS. 1 and 2.

The navigation menu 602 can include a plurality of sub-menus 630, 640 that can be expanded and contracted with a selection of a respective expand option 604. Within each sub-menu, values for each parameter associated with a category of information represented by that sub-menu can be viewed. In one example, the values can be viewed below the parameter name or rolled up and hidden with the selection of a first view option 606A provided next to each parameter name. For example, the readings sub-menu 630, when expanded, can display current values for $O_2$ saturation, pulse, respiratory rate, and head/body position A parameters 632, 634, 636, 638 where a first view option 606A is respectively selected for any of those parameters. Likewise, values for a simulation type 642, an elapsed time 644 for a current testing session, a force profile 646, and a risk profile score 648 may be view when the expand option 604 for the simulation details sub-menu 640 is expanded, and a first view option 606A is selected for any of those parameters as shown in FIG. 6.

A second view option 606B may be provided for those parameters for which the sensor or simulation control 210, 220 performs continuous monitoring during a testing session. Selection of the second view option 606B causes a graph charting the values for the corresponding parameter to be generated and continuously updated in the console window 608. For example, as shown in FIG. 6, a second view option 606B is selected for each of the 02 saturation, pulse, respiratory rate, and head/body position A parameters 632, 634, 636, 638. As a result, the console window displays a parameter sub-window 608A and results graph sub-window 608B for each. The parameter sub-window 608A may include a parameter name and current value for that parameter, whereas the results graph sub-window 608B charts values for that parameter for an entirety or selectable portion of a current simulation testing session.

In addition to the selectable options described above, the dashboard may include a subject address sub-menu 650 within the navigation window 602. The subject address sub-menu 650 may include a text field 652 in which an address of the subject may be entered. With an address entered in the text field 652, a map-based simulation option 680 may become active with the dashboard.

Selection of the map-based simulation option 680 may cause the simulation control 220 to access a service, such as the map service 250, and provide the address entered in the text filed 252. Further, selection may cause the simulation control 220 to request or direct the map service 250 to obtain possible routes that could be used to transport an infant to his or her address from a hospital where the infant is taking part in the simulation. The possible routes may then be transmitted to the simulation control 220 for analysis, simulation force patterning (e.g., magnitude and scheduling), and risk profile scoring. In one example, completion of the analyses will then cause a menu to appear in the dashboard that permits an operator to schedule a new simulation based on one of the routes returned by the map service.

The dashboard 600 also includes a get report option 684 and a stop simulation and alert option 688. An operator can select the get report option to access a summary of all recorded data for a current simulation. On the other hand, selection of the stop simulation and alert option 688 will stop an on-going simulation in manner determined to be safest for a subject. Thus, if in the process of reviewing the any of the values of any of the parameters in the navigation menu 602, or any of the results graphs in the console window 608, an operator believes continuing an ongoing simulation is unnecessary or presents a risk to a subject, the operator can stop the simulation almost immediately. In another example, where a stop condition is encountered during a simulation, as in stages 440A, 440B, 440C, or 440D, the dashboard 600 can be converted into or otherwise be modified to display an alert, a particular stop condition, and a notification that a current simulation is being stopped and the stoppage protocol being implemented.

Reference numerals and terminology used herein are for the purpose of describing particular aspects only and are not intended to be limiting. For example, as used herein, the singular forms—"a," "an," and "the"—are intended to include the plural forms as well, unless the context clearly indicates otherwise. As another example, recitation of ranges of values herein are merely intended to serve as a shorthand method of referring individually to each separate value falling within the range. Unless otherwise indicated herein, and each separate value is incorporated into the specification as if it were individually recited herein.

Furthermore, it is noted that any one or more aspects or features described with respect to one example, may be incorporated in different examples described herein, although not specifically referred to or otherwise described relative thereto. That is, all examples and/or features of any aspect described herein can be combined in any way and/or combination. Thus, all methods described herein can be performed in any suitable order unless otherwise indicated herein or otherwise clearly contradicted by context.

Other examples of the disclosure will be apparent to those skilled in the art from consideration of the specification and practice of the examples disclosed herein. Though some of the described methods have been presented as a series of steps, it should be appreciated that one or more steps can occur simultaneously, in an overlapping fashion, or in a different order. The order of steps presented are only illustrative of the possibilities and those steps can be executed or performed in any suitable fashion. Moreover, the various features of the examples described here are not mutually exclusive. Rather any feature of any example described here can be incorporated into any other suitable example. It is intended that the specification and examples be considered as exemplary only, with a true scope and spirit of the disclosure being indicated by the following claims.

What is claimed is:

1. A simulator for testing at least a cardiorespiratory stability of an infant during car travel, the simulator comprising:
 a car body;
 a back seat positioned within the car body;
 a base of a car seat assembly secured to the back seat;
 an infant seat of the car seat assembly secured to the base;
 a plurality of sensors configured to monitor parameters including:
  an oxygen saturation and a respiratory rate of a subject positioned in the infant seat, and
  a position of at least one of the infant seat relative to the base and the subject relative to the infant seat;
 a plurality of force applying actuators, each of the plurality of force applying actuators configured to apply one of a lateral, vertical, and linear force to a respective one of the back seat, the base, and the infant seat; and
 a control configured to operate the plurality of force applying actuators to apply lateral, vertical, and linear forces to the infant seat to simulate car travel relative to the subject,
 wherein the control is configured to access a map service with an address and generate a force application profile for a route provided by the map service based on the address, and
 wherein the control estimates forces to be applied to an infant car seat assembly in a vehicle traveling on the route.

2. The simulator of claim 1, further comprising a user interface configured to display values for the parameters as the control operates the plurality of force applying actuators.

3. The simulator of claim 2, wherein the user interface is mounted to the car body.

4. The simulator of claim 1, wherein the control includes a simulation control configured to operate the plurality of force applying actuators and a sensor control configured to operate and receive data from the plurality of sensors.

5. The simulator of claim 4, wherein the simulation control is configured to end the simulation based on values for the parameters indicating at least one of the respiratory rate is less than a first threshold, the oxygen saturation is less than a second threshold, and a deviation of the position from a neutral position is greater than a third threshold.

6. The simulator of claim 1, wherein the control is configured to determine a risk profile associated with the force application profile for the subject.

7. A car seat assembly for testing at least a cardiorespiratory stability of an infant during car travel, the car seat assembly comprising:
- a base configured to be secured to a back seat of a vehicle;
- an infant seat configured to be secured to the base;
- a first set of sensors configured to monitor parameters including an oxygen saturation and a respiratory rate of a subject positioned in the infant seat;
- a second set of sensors configured to monitor a position the infant seat relative to the base and a position the subject relative to the infant seat;
- a plurality of force applying actuators disposed in the infant seat and the base, each of the plurality of force applying actuators configured to apply one of a lateral, vertical, and linear force;
- at least one hub connected to the first set of sensors, the second set of sensors, and the plurality of force applying actuators; and
- a control configured to:
  - receive data from the first set of sensors and the second set of sensors,
  - access a map service with an address associated with the subject,
  - generate a force application profile for a route provided by the map service based on the address by estimating forces to be applied to the car seat assembly in a vehicle traveling on the route, and
  - determine a risk profile associated with the force application profile for the subject.

8. The car seat assembly of claim 7, wherein the control is configured to operate the plurality of force applying actuators to apply lateral, vertical, and linear forces to the infant seat to simulate car travel relative to the subject.

9. The car seat assembly of claim 8, wherein the hub puts the first set of sensors, the second set of sensors, and the plurality of force applying actuators in communication with the control.

10. The car seat assembly of claim 8, wherein the control is disposed in the base.

11. The car seat assembly of claim 8, wherein the control is configured to end a simulation based on values for the parameters indicating at least one of the respiratory rate is less than a first threshold and the oxygen saturation is less than a second threshold.

12. The car seat assembly of claim 8, wherein the control is configured to end a simulation based on a deviation of the position from a neutral position being greater than a threshold deviation.

13. The car seat assembly of claim 7, further comprising at least one adapter disposed in the base, wherein the at least one adapter connects a group of the plurality of force applying actuators disposed in the infant seat to the hub.

14. A method for testing at least a cardiorespiratory stability of an infant during car travel, the method comprising:
- providing a simulator including a car body, a back seat positioned in the car body, a base of a car seat assembly secured to the back seat, an infant seat secured to the base, a plurality of sensors, and a control;
- receiving, with the control of the simulator, subject information including a weight, a length, an age, and a gestational age at birth for a subject;
- generating simulation limits for a respiratory rate, oxygen saturation, and pulse of the subject for a simulation based on the subject information;
- positioning the subject in the simulator;
- checking, with the control and the plurality of sensors, vitals of the subject;
- implementing the simulation by operating, with the control, the plurality of force applying actuators to apply lateral, vertical, and linear forces to the infant seat;
- continuously monitoring the vitals of the subject during the simulation with the plurality of sensors;
- accessing, with the control, a map service with an address associated with the subject;
- generating, with the control, a force application profile for a route provided by the map service based on the address by estimating forces to be applied to the infant car seat assembly in a vehicle traveling on the route; and
- determining a risk profile associated with the force application profile for the subject.

15. The method of claim 14, further comprising:
- operating, with the control, the force applying actuators during the simulation based on the simulation limits and vitals of the subject detected by the plurality of the sensors; and
- displaying an elapsed time for the simulation and the vitals in a graphical user interface during the simulation.

16. The method of claim 14, further comprising:
- stopping, with the control, the simulation based on at least one of an elapsed time for the simulation and a comparison of the vitals of the subject and the simulation limits; and
- issuing, with the control, a stop alert.

17. The method of claim 16, wherein stopping the simulation includes:
- determining, based on the vitals detected by the plurality of sensors, the respiratory rate of the subject is less than a maximum threshold;
- operating, with the control, the plurality of force applying actuators to gradually reduce forces applied to the infant seat.

18. The method of claim 16, wherein stopping the simulation includes:
- determining, based on the vitals detected by the plurality of sensors, the pulse of the subject is less than a minimum threshold;
- operating, with the control, the plurality of force applying actuators to immediately stop applying forces to the infant seat.

* * * * *